United States Patent [19]

Shofner et al.

[11] Patent Number: 5,270,787
[45] Date of Patent: Dec. 14, 1993

[54] ELECTRO-OPTICAL METHODS AND APPARATUS FOR HIGH SPEED, MULTIVARIATE MEASUREMENT OF INDIVIDUAL ENTITIES IN FIBER OR OTHER SAMPLES

[75] Inventors: Frederick M. Shofner; Joseph C. Baldwin; Youe-T Chu, all of Knoxville, Tenn.

[73] Assignee: Zellweger Uster Inc., Knoxville, Tenn.

[21] Appl. No.: 493,961

[22] Filed: Mar. 14, 1990

[51] Int. Cl.$^5$ .................. G01N 21/00; G01N 15/14; G01L 5/04
[52] U.S. Cl. .................... 356/238; 73/160; 356/383; 356/385
[58] Field of Search ............... 356/383–387, 356/238, 430; 250/560; 73/160

[56] References Cited

U.S. PATENT DOCUMENTS

| | | | |
|---|---|---|---|
| 3,815,001 | 6/1974 | Duncan et al. | 356/167 |
| 4,027,162 | 5/1977 | Knollenberg | 250/345 |
| 4,377,746 | 3/1983 | Kopineck et al. | 356/430 |
| 4,978,859 | 12/1990 | Ransheim | 356/386 |

FOREIGN PATENT DOCUMENTS

| | | |
|---|---|---|
| 225001 | 6/1987 | European Pat. Off. . |
| 8802346 | 7/1988 | PCT Int'l Appl. . |
| 2064106A | 6/1981 | United Kingdom ........ 356/238 |

OTHER PUBLICATIONS

Steinkamp, "Flow Cytometry", Rev. Sci. Instruments, vol. 59, Sep. 1984, pp. 1382–1384.
Shofner et al, "Advanced Fiber Information System. A New Technology for Evaluating Cotton," Conference of the Textile Institute, 1988.
Faserforschung und Textiltechnik 25 (1974) Heft-12 Zeitschrift fur Polymerforschung (pp. 528–536).
Author: Frederick M. Shofner, Youe-Tsyr Chu (Mar. 15–17, 1990) Title: "An Overview of The Advanced Fiber Information System" 20th International Cotton Conference, Bremen, West Germany.
References: Bragg, C. K. (1988) "Advanced Technology for Measuring Cotton Fiber Length, Diameter, and Trash Content". 19th International Cotton Conference, Bremen, Germany. Faserinstitut Bremen e.V.
Sasser, P. E. (1988) "An Objective Method for Counting and Sizing Neps". 19th International Cotton Conference, Bremen Germany. Faserinstitut Bremen e.V.
Bragg, C. K. (1990), "A Rapid Measurement of Short Fiber Content". 20th International Conference, Bremen, Germany. Faserinstitut Bremen e.V.
Frey, M. (1990) "Practical Experience with New Cotton Measuring Methods." 20th International Cotton Conference, Bremen, Germany. Faserinstitut Bremen e. V.

(List continued on next page.)

Primary Examiner—Vincent P. McGraw
Assistant Examiner—K. P. Hantis
Attorney, Agent, or Firm—Luedeka, Hodges, Neely & Graham

[57] ABSTRACT

Single entities such as fibers are delivered one at a time to a fluid stream, and a nozzle orients the entities so that each entity along its length (major dimension) is generally parallel with the direction of fluid flow. The entity then enters a sample region and a sensor senses entity data such as the speed of the entity as it passes through the sample region. A preferred embodiment includes a collimated beam of light and two side-by-side photo detectors positioned to measure light extinction caused by fibers passing through the sample region. Another sensor may be provided to detect light scattered forward at an angle of about forty degrees (40°). The sensor signals are used to generate data that corresponds to such parameters as length, fiber ribbon width, fineness, cross-sectional area, maturity, cross-sectional circularity, shape, surface roughness, etc. Optical filtering provides information about composition (natural or man-made) and appearance (color and polarization).

20 Claims, 5 Drawing Sheets

OTHER PUBLICATIONS

Thibodeaux, D. P., and J. B. Price (1988). "An Absolute Reference Method and Determination of the Maturity of Cotton Fibers", 19th International Conference, Bremen, Germany. Faserinstitut Bremen e. V.

Thibodeaus, D. P. (1990). "Update on Special Applications of Cotton Maturity Testing". 20th International Cotton Conference, Bremen, Germany. Faserinstitut Bremen e.V.

Shofner, F. M., G. F. Williams, C. K. Bragg, P. E. Sasser (1988). "Advanced Fiber Information System: A New Technology for Evaluating Cotton", Conference of the Textile Institute, Coventry, UK.

Sasser, P. E., F. M. Shofner, Y. T. Chu, C. K. Shofner, M. G. Townes (1990). "Interpretation of Single Fiber, Bundle, and Yarn Tenacity Data." Submitted for publication to *Textile Research Journal*.

Deussen, H. and L. Neuhas (1988). "Why does the Need for Finer, Stronger, and Cleaner Cotton Fibers Require a Change in the Cotton Grading and Marketing System?", W. Schlafhorst & Co., Documentation No. 21, Monchengladback, West Germany.

Lord, E. and S. A. Heap (1988). "The Origin and Assessment of Cotton Fibre Maturity." Published by the Technical Research Division, International Institute for Cotton, Manchester, UK.

ELECTRO-OPTICAL METHODS AND APPARATUS FOR HIGH SPEED, MULTIVARIATE MEASUREMENT OF INDIVIDUAL ENTITIES IN FIBER OR OTHER SAMPLES

FIELD OF THE INVENTION

The present invention relates to an apparatus and method for measuring characteristics of single entities and particularly relates to measuring the speed, length, width characteristics and surface characteristics of single fibers in a fluid flow.

BACKGROUND OF THE INVENTION

Demands for more and better information on fiber properties have steadily risen from the beginning of the industrial revolution until today. Production rates of textile processing machinery have dramatically increased, especially in the past 25 years. Tolerances for variations in fiber properties have, correspondingly, dramatically decreased as speed and quality demands have risen. To achieve better control over quality, while increasing production speed, represents a major challenge for modern manufacturing, a challenge which can only be met with improved information, in vastly increased quantities, about the raw materials of textile manufacturing, fibers, both natural (cotton, wool, etc) and man-made (polyester, nylon, etc.).

These observations about modern textile manufacturing apply as well to modern aerosol manufacturing. Production rate increases and decreases in tolerance for variations in particular sizes demand more and better information as well.

Accordingly, this invention is in the field of electro-optical measurement of the physical properties of fibers and aerosols; the invention is part of and enables a system whereby heretofore impossibly accurate, precise, reliable, fast, and cost-effective information can be generated on a wide variety of physical properties of fibers and aerosols.

A brief historical overview of prior art in the fiber testing will clarify the relation of this system to it and especially the major improvements this invention makes in fiber testing. A similar overview could be set forth for aerosol testing.

In the mid-1800s, when only natural fibers were available, the revolutionary technology of that period, water-or steam-powered machinery, already demanded more and better information.

Standards for cotton, for example, were established and cotton classers or graders painstakingly learned and applied their trade to assure that "smooth and even-running" lots were delivered to the mills. The Liverpool Staple Standards became the most widely used until, in the early 1900's, the United States Department of Agriculture began to dominate, world-wide, the definition, preparation, and supply of standard cotton materials, which they do even today.

In the 1960's, in response to demands for more and better information, the USDA began to consolidate developments in instrumental fiber testing. One approach, conducted by Stanford Research Institute for the USDA, was to measure cotton fiber length and diameter electro-optically. The fibers were individually presented to the measurement zone by a combination of aerodynamic and electro-static forces. Severe difficulties with the generation and the presentation of single fibers and low data rate, less than 1 fiber/second, led to abandonment of this approach.

The successful approach to so-called "High Volume Instrument" lines simply used faster-operating versions of already-existing laboratory instruments. These instruments indirectly measure fiber length, strength, diameter, and color. Prototypes were completed by the mid-1970's but the technology was rejected by certain parties in the trade and lay dormant until 1980 when pressure from dissatisfactions with manual classing caused farmers in Lamesa, Tex. to insist on HVI. Today about 50% of US cotton is classed by HVI; by 1992, almost 100% will be. It is expected that most of the world cotton crop will be instrument-classed by around the year 2000, not necessarily with current-generation, but with improved fiber testing instrument technology, some of which is the subject matter of this invention.

The basic technology for current generation HVI measurements is 25-75 years old except for the computers used to automate them and to process the data. It is becoming clear, unfortunately, that these older test methods do not and cannot provide the advanced fiber information, the "more and better information" required by modern textile processing.

Two or more operators are required and testing time averages about ½ minute. Never-the-less, current generation HVI has enabled a major marketing breakthrough.

It was recognized in the early 1980's that Research and Development upon the next generation HVI must begin as soon as possible and even before HVI was widely accepted or even widely known. The concept advanced by the first-named inventor of this invention, that of measuring, directly and at high speed, physical properties of single entities in the fiber sample, were accepted by forward-looking leaders in fiber testing and marketing as a candidate technology. These more basic measurements provide the more and better information needed by modern textile manufacturing. They are more basic because single entities (single fibers, single neps, single trash particles, single microdust particles, etc.) are directly measured rather than indirectly by measuring bulk or bundle properties.

Equally importantly, they are more basic because statistical distributions are easily formed with the aid of modern electronics technology.

These concepts led to various prototype systems that are called the Advanced Fiber Information Systems (AFIS) and consist of: (1) aeromechanical separator or fiber individualizer, (2) high speed, single entity sensors, and (3) high information rate, personal-type computer. Only the latter is well-known in the art of modern electronics.

The aeromechanical separator is described in U.S. Pat. Nos. 4,512,060; 4,631,781; and 4,686,744.

Sensor means for single fiber strength measurement are described in co-pending U.S. application "Fiber Testing Apparatus and Method", Ser. No. 07/460,292.

Prior art electro-optical sensors are described in U.S. Pat. Nos. 4,249,244; 4,396,286; 4,473,296; and 4,885,473.

For AFIS fiber testing applications, various open literature contributions have been made such as:

1. "Advanced Fiber Information Systems: A New Technology for Evaluating Cotton":, by F. M. Shofner, G. F. Williams, C. K. Bragg, and P. E. Sasser (December 1988 presented at the Textile Institute Conference Fiber Science Group, U.K.).

2. "Advanced Technology for Measuring Cotton Fiber Length, Diameter, and Trash Content" by C. K. Bragg (March 1988).

3. "An Objective Method for Counting and Sizing Neps" by P. F. Sasser (March 1988).

For simplicity, we refer to our prior art, prototypical, electro-optical (E-O) fiber testing technology and embodiments as AFIS 0. AFIS 0 included a fiber individualizer, a fluid stream, a nozzle for accelerating the fluid stream, a converging beam of light and a forward light scattering detector. It did not include, among other things, a speed sensor, an extinction mode sensor or a substantially collimated beam of light. We refer to the improved E-O technology for fiber and aerosol testing of this invention as AFIS 1. It will be seen that AFIS 1 provides new data products, some previously impossible, and new E-O means, over AFIS 0.

Practical experience with AFIS 0 demonstrated that the concepts of high speed measurement single entities, followed by calculation of statistical distributions, are urgently needed. Prior art measurements are increasingly seen as inadequate and even misleading for modern textile manufacturing. Indeed, recently-accelerating demands for more and better information provided the motivation to research and to develop these AFIS 1 improvements over AFIS 0, which itself already provided improvements over current-generation HVI.

Accordingly, it is the broadest objective of this invention to provide improved fiber and aerosol measurements over prior art, including AFIS 0. The improvements are in all major categories of accuracy, precision, reliability, speed, and cost-effectiveness. Most importantly, the E-O improvements herein disclosed provide more basic information than previously possible.

Another objective is to provide a fiber testing system and method which, in combination with other features and measurements, such as single fiber strength or color, enables a single operator HVI System with test zone environmental control and which can ultimately operate at test times of ¼ minute.

A further objective is to provide aerosol testing apparatus and methods which enable laboratory quality control instruments or ultimately, on-line, closed-loop control systems for aerosol manufacturing.

Another objective is to provide monovariate statistical distribution information on at least these entities in fiber samples: length, diameter, fineness, maturity, color, shape, surface roughness, for the fibers themselves; neps; trash particles; dust and microdust particles. Neps, trash, dust and microdust are regarded as undesirable elements in the fibrous mass.

Yet another objective is provision of multivariate statistical distribution information as, for example, bivariate distributions in fiber length and diameter or trivariate distributions in particle diameter, shape, and surface roughness.

Whereas the broader user-related objectives provide for more and better information on physical characteristics of fibers or aerosols, a more specific objective of this electro-optical invention is to enable measurement of fiber or aerosol speed and acceleration in the scattering zone and to use this data to provide more absolute readings of length and improved readings of other physical characteristics such as diameter, fineness, maturity, color, shape, and surface roughness and the like.

A still further objective of the invention is to provide for simultaneous measurement of 2 or more scattering angles.

A similar further objective is to provide for measurements using simultaneously-emitted electromagnetic radiation components having 2 or more principal or mean wavelengths and 2 or more states of polarization.

The ultimate objective is to optimally combine these new electro-optical sensor means with suitable fiber or aerosol individualizer means and modern electronics means into systems which provide more and better fiber or aerosol information, as demanded by modern manufacturing.

SUMMARY OF INVENTION

In accordance with the present invention, an apparatus is provided for rapidly measuring the properties of single entities such as fibers. The apparatus includes a source of single entities and a fluid stream. Single entities are delivered one at a time from the source to the fluid stream and means are provided for orienting the entity so that each entity along its length (major axis) is generally parallel with the direction of the fluid flow and, thus, has a leading entity end and a trailing entity end. A sample region is disposed in the fluid stream downstream of the orienting means and at least one sensor is disposed in the sample region for sensing characteristics of each entity as it passes through the sample region. In the preferred embodiment at least a speed sensor is provided to detect the speed of entities.

The apparatus may further include means for sensing the time at which the leading end of each entity passes a selected point in the sample region and for sensing the time at which the trailing end of each entity passes the same selected point. Means are also provided for determining the time differences between when the leading end passes the selected point and when the trailing end passes the selected point and for calculating the length of each entity based on the speed of the entity and the time difference.

It has been discovered that entity speed varies significantly when comparing one entity to another. It has been further discovered that the entities are actually accelerating even in the sample region and for many purposes it is not sufficient to measure the speed of the entity just once while it is in the sample region. Thus, the speed sensor includes a collimated beam of light disposed to pass through the sample region and a first light sensor disposed adjacent to the sample region for receiving light from the collimated beam of light. A second light sensor is also disposed adjacent to the sample region for receiving light from the collimated beam of light, and the first and second light sensors are spaced apart one from the other by a predetermined distance. The second light sensor is positioned downstream from the first light sensor, relative to the fluid flow, but not necessarily in the fluid flow, and the first and second light sensors are dimensioned and positioned to detect the extinction of light caused by entities passing through the sample region. The first light sensor detects when the leading end of each entity passes a first point in the sample region and the second light sensor determines when the leading end of the entity passes a second point in the sample region downstream of the first point. In like manner, the first sensor detects when the trailing end of the entity passes the first point and the second sensor detects when the trailing end of the entity passes the second point in the sample region. Electronics connected to the first and second sensors first determines a leading time for each entity passing through the sample region where the leading time corresponds to the time required for the leading end of each entity to pass from the first point to the second point. Likewise, the electronics determines a trailing time for each entity where the trailing time corresponds to the time required for the trailing end of each entity to pass from the first point to the second point. The distance between the measurement points represents not the physical dimensions of the detectors, but the object space formed by the optical system. This equal interaction distance can be changed by the optical system to accommodate various ranges of velocities and particle sizes and can be calibrated by independent means to the required accuracy.

Since the effective distance between the first and second sensors is known and it is known that the light beam is collimated, the distance between the first and second points is also known. Thus, the speed of the leading end of the fiber is determined by dividing the distance between the first and second points by the leading time. Likewise, the speed of the trailing end of the fiber is determined by dividing the distance between the first and second point by the trailing time. In the preferred embodiment the fibers are generally accelerating and the speed of the trailing end will be faster than the speed of the leading end. Thus, a mean fiber speed is determined by averaging the speeds of the leading end and trailing end of the fibers or by averaging the leading and trailing times or by other mathematical means based on the leading and trailing times.

It has also been determined that the signals generated by the first and second sensors exhibit characteristic peaks and valleys corresponding to physical attributes along the fiber. By comparing the peaks and valleys of the first sensor signal to the peaks and valleys of the second sensor signal, one may calculate numerous speeds of the fiber at different points in time and space and, thereby, determine to a high degree of accuracy the acceleration and actual speed of the fiber during its flight past the sensors. Thus, the leading and trailing ends of the fiber should be considered two of many physical features of the fiber that may be observed to measure fiber speed.

The signals received from the first and second sensors also contain information as to the amount of light extinguished by the fiber and this information corresponds to the ribbon width of the fiber. Since most cotton fibers are not circular they will not have a uniform width when viewed from one side. Rather, they will appear more like a twisted ribbon and, thus, the width of the fiber will vary depending upon the angle at which it is viewed. However, as the fiber passes through the sample chamber, an average or mean ribbon width may be determined by observing the amount of light extinction caused by the fiber as it passes through the sample chamber.

In addition to the first and second light sensors, a third light sensor may be disposed for receiving light scattered forward by the fiber at a forward scattering angle of about forty degrees (40°) with respect to the direction of the collimated beam of light. The forward light scattering contains information as to the surface properties of the fiber, and in particular, the forward light scattering corresponds well to the micronaire value for the fiber and, therefore, corresponds to fiber circularity and fiber maturity. The first and second sensors provide extinction mode signals and they correspond proportionately with the micronaire value of a fiber and inversely with circularity and maturity. Thus, by using combinations of the signals from the first or second signals and the third sensor (extinction and scattered modes combined) one may generate signals corresponding to circularity, cross sectional area, maturity, geometric shape and other related parameters. Through the use of filter elements in the optical path of scattered light one may also resolve color properties and light polarization properties of the individual fibers. Preferably, fourth sensors are provided to detect back scattered light from individual fibers and these sensors are used in combination with appropriate filters to ascertain color characteristics of the fiber.

BRIEF DESCRIPTION OF THE DRAWINGS

The present invention may best be understood by reference to a Detailed Description of preferred embodiments when considered in conjunction with the DRAWINGS in which:

FIGS. 2a and 2b are somewhat diagrammatic side views of the sensor and sample region of the apparatus in which FIG. 2b is rotated in a horizontal plane approximately ninety (90°) degrees with respect to FIG. 2a;

DETAILED DESCRIPTION OF PREFERRED EMBODIMENT

Figure 1:
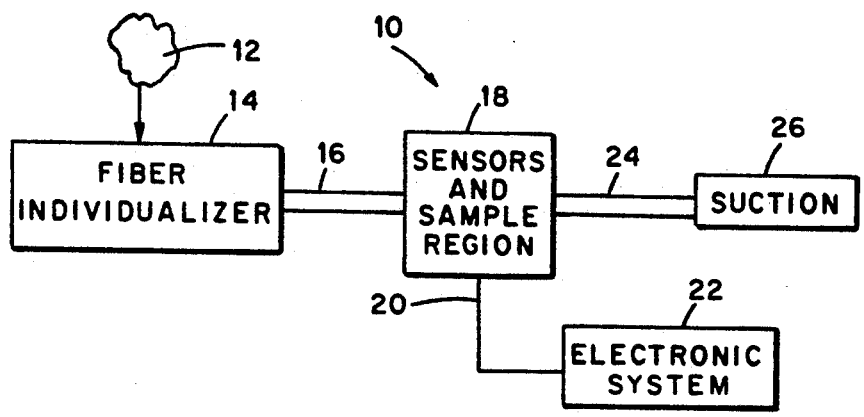
FIG. 1 is a block diagram of the single fiber measuring apparatus.

Referring now to the drawings in which like reference characters designate like or corresponding parts throughout the several views, there is shown in FIG. 1 a block diagram of apparatus 10 which constitutes a preferred embodiment of the present invention. Although this apparatus 10 is intended for measuring fibers, it will be understood that the apparatus 10 also measures properties of non-fiber entities such as aerosols. As used herein, the term entity refers to a fiber and/or a non-fiber particle. A fiber sample 12, such as a sample of cotton, is provided to a fiber individualizer 14 which separates single fibers from the sample 12 and delivers the single fibers to a conduit 16. The fiber individualizer 14 is manufactured by Zellweger Uster of Knoxville, Tenn. as part of the AFIS 0 system. A fluid stream, preferably an air stream, is formed in the conduit 16 flowing from the fiber individualizer 14 to a sensor and sample region 18. Thus, the conduit 16 delivers single fibers, one at a time, to the sensor and sample region 18 wherein the fibers are sensed and electronic signals are generated corresponding to properties of each fiber. These signals are transmitted through lines 20 to an electronic system 22 that conditions and analyzes the signals and stores information corresponding to received signals which also correspond to the properties of the fibers being analyzed.

A conduit 24 extends between the sensor and sample region 18 and a suction source 26. The suction source 26 applies a suction to the conduit 24 which in turn creates a suction in the region 18 and the conduit 16 thereby creating the fluid stream.

Figure 2A:
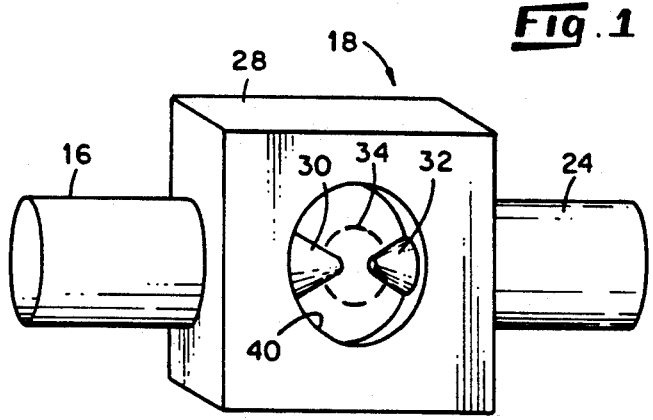

Referring now to FIG. 2a, there is shown a somewhat diagrammatic side view of a portion of region 18. A nozzle block 28 is provided for holding a pair of nozzles 30 and 32 in a spaced apart facing relationship. Nozzle 30 is connected to receive fluid flow and fibers from conduit 16 and is referred to herein as an accelerating nozzle 30 because the fluid and fibers are accelerated as they pass through nozzle 30. In a similar manner, nozzle 32 is connected with conduit 24 and is referred to herein as a decelerating nozzle 32 because fibers and fluid are decelerated as they enter into the nozzle 32. Nozzles 30 and 32 are facing one another at their tapered ends so that the suction applied by the conduit 24 creates a fluid flow that is aligned with the conduits 24 and 16 and is aligned with the center axes of the conically shaped nozzles 30 and 32, since the nozzles 30 and 32 are aligned, the accelerated fibers exit the accelerating nozzle 30, travel directly across the gap between the nozzles 30 and 32 and enter the decelerating nozzle 32.

Also illustrated in FIG. 2a is a beam of collimated light 34 that illuminates the gap between the nozzles 30 and 32. The gap between nozzles 30 and 32 is sometimes herein referred to as the measurement zone.

Figure 2B:
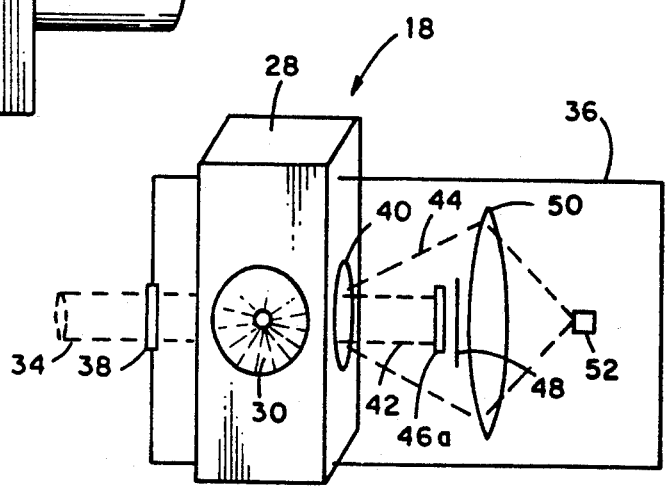

Referring to FIG. 2b, additional details of the sensor and sample region are shown diagrammatically. The region 18 includes a sample chamber 36 that seals the area around the nozzles 30 and 32 (FIG. 2a) so that the suction provided by the conduit 24 (FIG. 1 and 2a) creates fluid flow in the nozzle 30 and conduit 16 (FIGS. 1 and 2a). A collimated beam of light 34, preferably having a wavelength of 880 mm, enters the sample region 36 through an optical window 38 formed therein. The collimated beam of light 34 then passes through the aperture 34 which is formed in the block 28 and impinges upon the gap between the nozzles 30 and 32 (best shown in FIG. 2a). The fibers that pass between the nozzles 30 and 32 will cause extinction of some of the light of the collimated beam 34 and will cause scattering of the light. Zero degree forward scattering of the light is illustrated by the dashed lines 42 and forward scattering caused by the fibers at an angle of about forty (40°) degrees is illustrated by the dashed line 44. Zero degree forward scattered light is primarily indicative of the light extinction caused by the fibers and extinction sensors such as light sensor 46a are disposed to receive and sense such zero degree forward scattered light. Although there are two extinction sensors, only the one sensor 46a is shown in FIG. 2b and the other sensor is hidden behind sensor 46b. A circular shield 48 and a lens 50 are disposed behind the extinction sensor 46a and are operable to collect and focus the forty (40°) degree scattered light 44 onto a light sensor 52.

Figure 3:
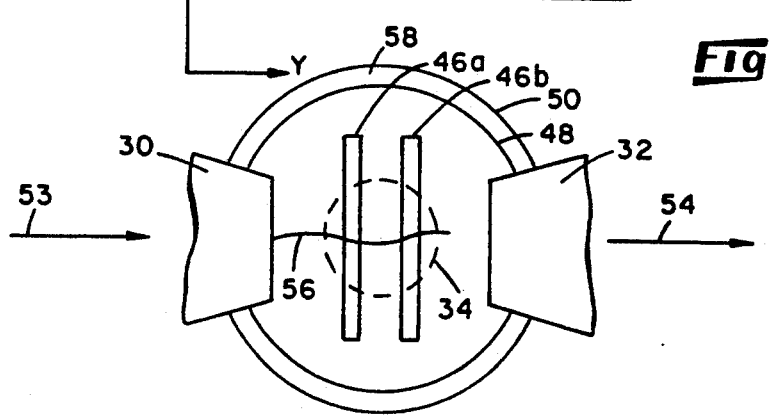
FIG. 3 is a partial diagrammatic view of the nozzles and sensors that are disposed in the sample region.

A plan view of the sensors 46a and 46b are shown in FIG. 3. In this view, the fluid flow is indicated by arrows 53 and 54 and a fiber 56 is shown exiting the nozzle 30 and passing in front of the sensors 46a and 46b. It should be noted that the collimated light beam 34 impinges upon the fiber 56 in the area immediately in front of the sensors 46a and 46b. Thus, sensors 46a and 46b will respond to the full intensity of the collimated light beam 34 in the absence of any fibers disposed in the beam 34 and, in the presence of fibers in the beam 34, the sensors 46a and 46b will receive the full intensity of the light beam 34 less the amount of light extinction caused by the fiber 56 and less the amount of light scattered around the sensors 46a and 46b by the fiber 56. In practice, the reduction in light received by the sensors 46a and 46b in the presence of a fiber 56 will be primarily due to the extinction of light caused by the fiber 56.

Also shown in FIG. 3 is the circular shield 48 and the lens 50. It will appreciated that the shield 48 and lens 50 form an annular aperture 58 that receives forward scattered light at an angle of about forty (40°) degrees with respect to the direction of the collimated beam 34 wherein the forty (40°) degree angle is rotated three hundred and sixty (360°) degrees about the directional axis of the collimated beam 34.

Figures 4, 5:
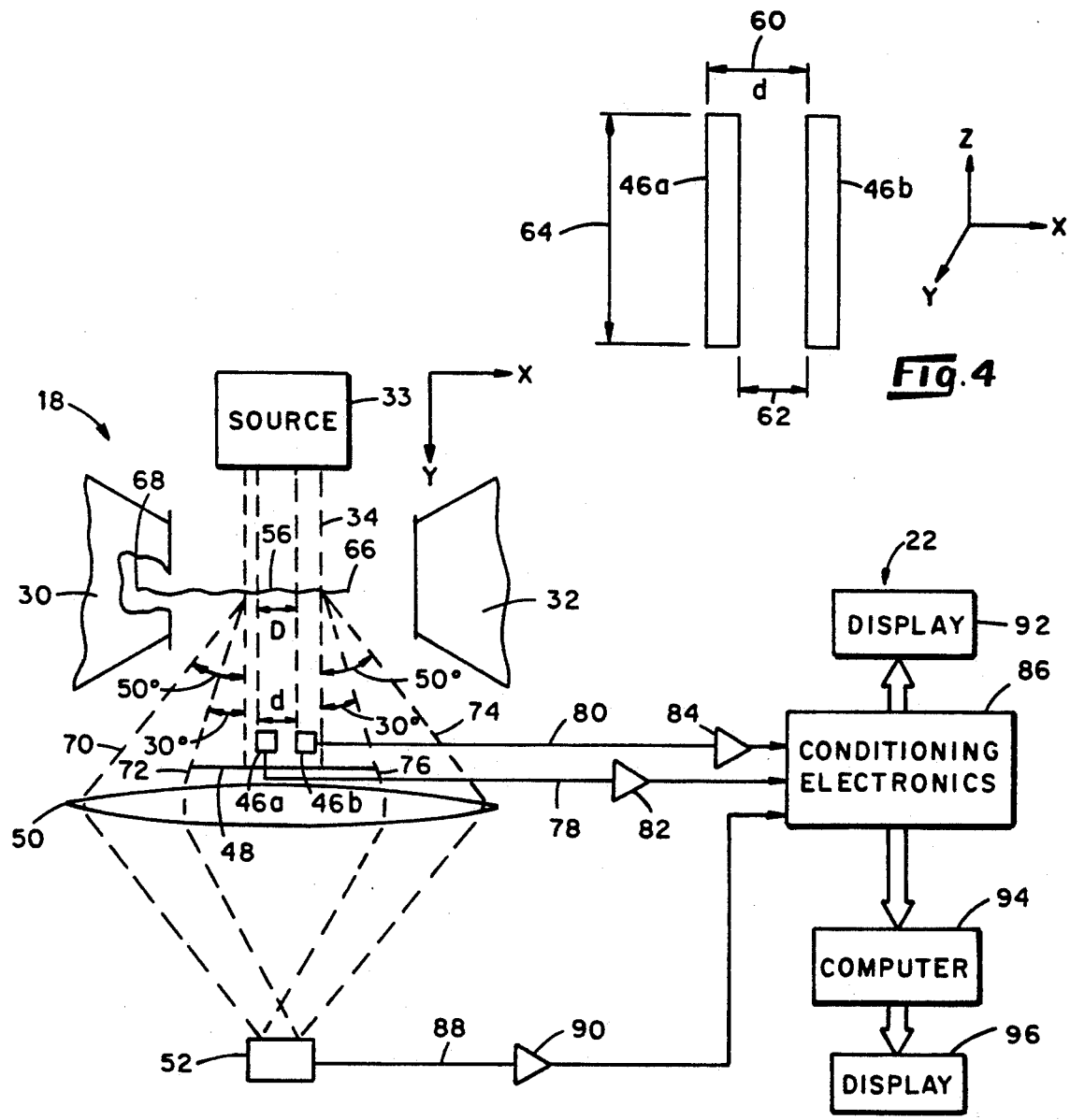
FIG. 4 is an illustration of two spaced apart extinction sensors used in the sensor and sample region of the apparatus.
FIG. 5 is a diagrammatic plan view illustrating the operation of the sensors and the interconnection of the sensors with conditioning electronics and a computer.

Referring to FIG. 4, detailed views of sensors 46a and 46b are shown. The sensors 46a and 46b are matched solid state photo detectors that are manufactured on a single chip by Silicon Detector Corp. As shown in FIG. 4, the distance 60 between the left edge of sensor 46a and the left edge of 46b is 530 microns. Likewise, the distance between the centers of sensors 46a and 46b and the right edges of sensors 46a and 46b is also 530 microns. The distance 62 between the right edge of sensor 46a and the left edge of sensor 46b is approximately 20 microns, and the distance 64 between the tops and bottoms of the sensors 46a and 46b is 4.57 millimeters.

Sensors 46a and 46b are used primarily to detect light extinction caused by the fibers, such as fiber 56 shown in FIG. 3. However, it is not intuitively apparent that the sensors 46a and 46b would be capable of measuring such extinction with sufficient accuracy to determine the position of fiber 56. Typically, a cotton fiber has a ribbon width of approximately 20 micrometers. Because of this small ribbon width, when light impinges upon the cotton fiber, it rapidly diffracts behind the fiber and creates a diffuse diffraction pattern. In other words, because the fiber is so small, it does not cast a shadow with sharp edges as one might expect with a larger object. The diffraction pattern or the near zero degrees forward scattered light does not resemble a shadow in the ordinary sense of the word. But an ordinary sharply-defined shadow is not as important here as having identical, symmetrical, and constant responses from the two detectors. We discovered that the sensors 46a and 46b can so respond if the beam intensity is substantially constant over the spatial extent of the detectors. We have further discovered that the effective spacing D (see FIG. 5) as measured between the nozzles 30 and 32 in the measurement zone can be adjusted precisely by causing the light beam to slightly diverge (D<d) or converge (D>d) (see FIGS. 4 and 5) as the beam moves in the +Y direction toward the detector pair.

As the fiber or other entity moves in the +Y direction extinction caused by the fiber or other entity produces a symmetrically equal response whose difference in time corresponds exactly to the difference in space D. Thus speed is measured. The sensors 46a and 46b will, in fact, detect the extinction caused by the fibers with sufficient accuracy to enable one to determine the presence of the leading and trailing edges of the fiber and the presence of other physical characteristics of the fiber. In other words, even though the diffraction and extinction effects of the fiber may be spread over a relatively large region of the sensors 46a and 46b as compared to the ribbon width of the fiber, the sensors 46a and 46b are still capable of producing signals indicating when the leading and trailing edges of the fibers pass in front of the sensors 46a and 46b. Also, the signals from the sensors 46a and 46b may be compared based on peaks and valleys in the two signals and, thus, the speed of the fiber may be repetitively calculated for different positions of the fiber in time and space.

It will be appreciated that the dimensions of the sensors 46a and 46b are relatively small in a direction parallel to the travel of the fibers. However, in a direction perpendicular to the travel direction of the fibers, the sensors have a relatively large dimension which will enable the sensors to sense light extinction even if the fibers do not pass through the same general area each time. Also, even though the diffraction pattern created by a sensor may be much larger than the fiber itself, the entire pattern will still fall on the sensors 46a and 46b, at least in a direction perpendicular to the travel of the fiber. In other words, the fibers will be traveling in the x-direction as indicated in FIG. 4, and the diffraction pattern created by the fiber will be blurred and magnified in the z-direction. However, because of the relatively large dimensions of the sensors 46a and 46b in the z-direction, as compared to the fiber ribbon width, the fiber diffraction pattern or the x-dimension of sensors 46a and 46b, the sensors will still receive the extinction data along the z-direction. It is the receipt of this extinction data in the z-dimension that allows detection of physical features of the fiber with sufficient resolution to enable precise timing of the fiber flight.

Referring now to FIG. 5, there is shown yet another diagrammatic view of the sensor and sample region 18 and electronics system 22. In this view, it may be appreciated that the fiber 56 has a leading end 66 and trailing end 68. When the leading end 66 first enters the beam 34, it scatters light and causes light extinction. Referring to FIG. 5, the dashed line 70 represents light that is scattered by the fiber 56 from the left-most side of the beam 34 at a forward scattering angle of fifty (50°) degrees. In like manner, dashed line 72 represents thirty (30°) degree forward scattered originating at the left side of the light beam 34. Dashed line 74 represents fifty (50°) degree scattered light originating at the right side of the beam 34 and dashed line 76 represents thirty (30°) degree scattered light originating at the right side of beam 34. The light between dashed lines 70 and 72 and between dashed lines 74 and 76 is collected by the lens 50 and focused upon the sensor 52. Thus, the lens 50 will collect forward scattered light in an annular pattern as best shown in FIG. 3 that is scattered at an angle of between thirty and fifty degrees.

Light that is scattered by the fiber 56 from the center of the beam 34 will have scattering angles that are greater than fifty degrees. However, the apparatus illustrated in FIG. 5 is intended to illustrate what applicants consider to be approximately forty degree forward scattered light.

As shown in FIG. 5, the light detected by sensors 46a and 46b is converted into electrical signals which are transmitted through lines 78 and 80 to amplifiers 82 and 84 and then to conditioning electronics 86. In a similar manner, the light that is focused by the lens 50 onto the sensor 52 is converted to an electrical signal which is transmitted through line 88 and amplifier 90 to the conditioning electronics 86.

In the case of the signals received from the sensors 46a and 46b, the electronics 86 are conditioned to detect decreases in voltages which correspond to the extinction of light caused by fibers 56 passing in front of the sensors 46a and 46b. The signal received from the sensors 46a and 46b may be displayed in the analog domain on display 92 which, preferably, is an oscilloscope. Also, the signals are converted to digital form and are transmitted to the computer 94 where they are stored and further analyzed. A display 96 is also connected to the computer 94 so that visual displays may also be generated from the digital data corresponding to the signals from sensors 46a and 46b.

The signal from sensor 52 will increase in voltage in the presence of a fiber 56 which is opposite to the effect that the fiber 56 has on the light received by sensors 46a and 46b. Thus, the conditioning electronics 86 is adapted to detect increases in the voltage of the signal from the sensor 52. As before, the signals from sensor 52 may be shown on display 92 in the analog domain and are converted to digital form and stored in the computer 94. Again, the digital data corresponding to the signals from the sensor 52 may be shown on display 96.

Figure 6:
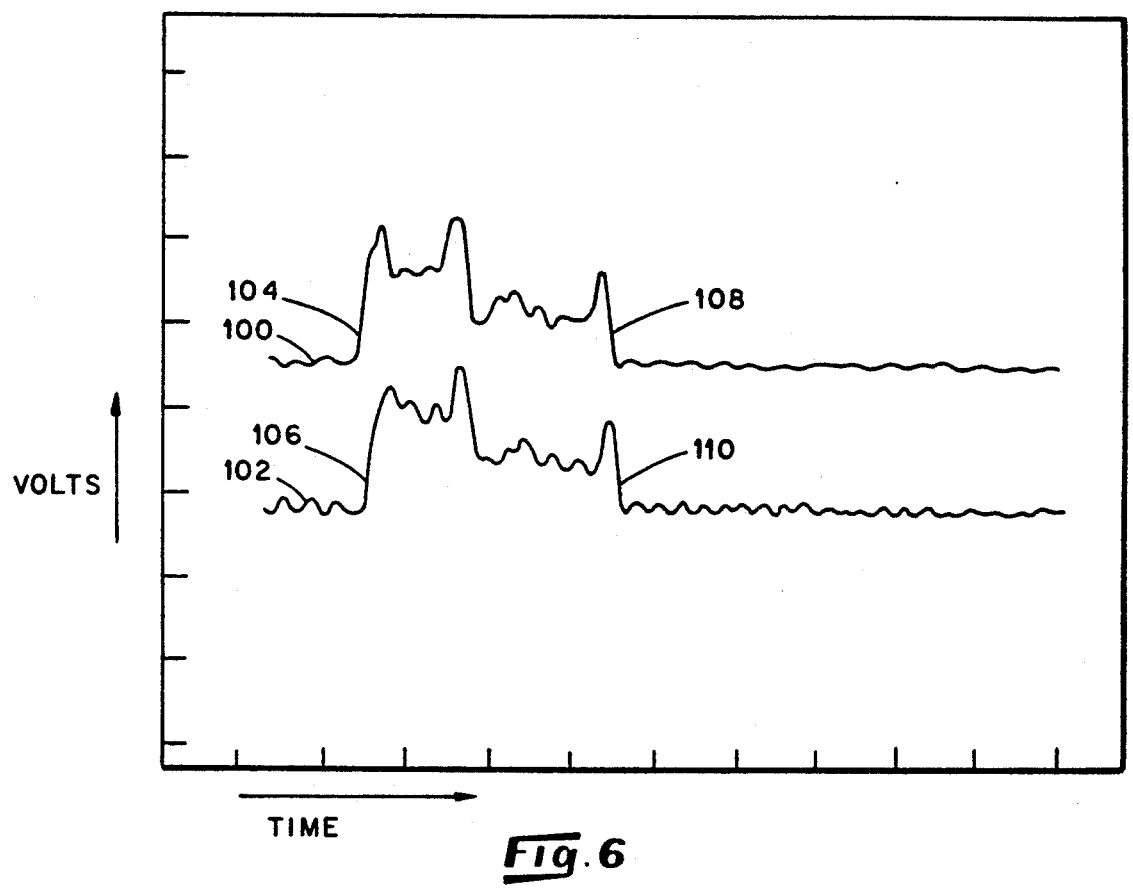
FIG. 6 is a graph of typical signals produced by two extinction sensors when a fiber passes in front of them.

Referring to FIG. 6 in conjunction with FIG. 5, the operation of the apparatus 10 may best be understood. FIG. 6 shows an oscilloscope display of two signals 100 and 102 that represent signals received from the sensors 46a and 46b, respectively. The y-axis of the graph represents the voltage of the signal and x-axis of the graph represents time. Although signal 100 is shifted significantly above signal 102, it should be understood that the base line voltages of two signals are very nearly the same. However, the graph of signal 100 has been shifted upwardly with respect to the graph of signal 102 for the purpose of illustration. In other words, the zero base line of signal 100 is significantly above the zero base line of signal 102.

When the leading end of the fiber 56 begins to cross in front of sensor 46a, the graph of signal 100 rises rapidly and after the signal has risen to a predetermined level, indicated by reference character 104, one assumes that the leading end of the fiber is passing a predetermined point in space immediately in front of the detector 46a. Likewise, when the signal 102 increases to a predetermined voltage indicated by reference character 106, the leading end of the fiber is positioned at a predetermined point immediately in front of the sensor 46b. The reference characters 104 and 106 indicate points on the two graphs that are the same predetermined voltage above a zero voltage reference line for the particular graph, and it will be appreciated that the signal 100 reaches the predetermined level indicated by character 104 slightly before signal 102 reaches the predetermined level indicated by character 106. This difference represents the time that is required for the leading end of the fiber to travel from a predetermined point in front of the sensor 46a to a corresponding point in front of the sensor 46b.

In like manner, when the signal 100 drops below a predetermined reference level indicated by character 108, the trailing end of the fiber is positioned at a predetermined point in front of the detector 46a, and when the trailing end of the fiber 56 is positioned at a corresponding point in front of the detector 46b, the voltage of signal 102 drops to the point indicated by character 110.

The difference in time between the positions indicated by characters 108 and 110 represents the time required for the trailing end of the fiber 56 to travel from a predetermined point in front of sensor 46a to a corresponding point in front of sensor 46b. Also, by observing the characteristic peaks and valleys of the two signals, it will be observed that the peaks and valleys of signal 100 occur before the peaks and valleys of the signal 102. These peaks and valleys represent physical characteristics of the fiber and the occurrence of the peak in signal 100 indicates that a particular physical feature has appeared in front of the sensor 46a. Then, the corresponding peak or valley in signal 102 indicates that the same physical feature has appeared in front of the sensor 46b. By comparing the time positions of the peaks and valleys as between signals 100 and 102, one may again calculate the time required for these physical characteristics to pass from the sensor 46a to the sensor 46b.

It has been discovered that the fiber in the above-described apparatus is accelerating as it passes between the nozzles 30 and 32 and passes in front of the sensors 46a and 46b. Since the fiber is accelerating, it takes less time for the trailing end of the fiber to travel the same distance as the leading end of the fiber. This phenomenon may best be observed by reference to FIG. 7 in which the signals from sensors 46a and 46b are superimposed one on top of the other. In this view, two corresponding peaks in the two curves are generally indicated by the reference character 112. These two peaks represent a physical characteristic near the leading end of the fiber. Likewise, two other corresponding peaks in the two curves are indicated by reference character 114 and these two peaks would represent a physical characteristic of the fiber near its trailing end. It will noted that the two peaks indicated by character 112 are further apart than the peaks indicated by the character 114. This means that the leading end of the fiber requires greater time than the trailing end of the fiber to travel the same distance. Thus, the leading end of the fiber was traveling more slowly when it passed sensors 46a and 46b than the trailing end of the fiber. By measuring the time distance between corresponding peaks in the two signals all along the signals, one may accurately determine the actual speed of the fiber at different time and space positions and acceleration is calculated by the computer 94 based upon the change in speed and the time between the two measurements based upon the knowledge that the change in speed equals acceleration multiplied by time. It has been discovered that the acceleration of the fiber is not linear; it is slightly parabolic. However, the acceleration is sufficiently close to linear that the length of a fiber can be accurately determined by measuring the leading end speed, the trailing end speed and averaging the two speeds to determined a mean speed of the fiber. In order to determine the length of a fiber, one first determines the time difference between when the leading end passes a particular point in front of one of the sensors 46a or 46b and when the trailing end passes that same point. Multiplying this time difference by the mean speed will produce a product that is equal to the length of the fiber.

Another method of finding the fiber speed is to determine the times required for the leading end to travel from a point in front of sensor 46a to a point in front of sensor 46b (the leading end time) and to determine the time required for the trailing end to pass between the same two points (the trailing end time). Then, the leading end time and trailing end time are averaged to determine an average time. Fiber speed is then determined by dividing the distance between the two points by the time average. Since the acceleration of the fiber is not constant, the average or assumed fiber speed differs depending on which of the above two methods are used to calculate speed, but either is more accurate than assuming constant speed or measuring speed once. Also, other mathematical models may be used to predict average speed, fiber speed or fiber length based on two or more time measurements.

Referring again to FIG. 6, it has been further discovered that the integrated area beneath the graphs of signals 102 and 104 corresponds well to the average or mean ribbon width of the fiber. In other words, the average amplitude of the signal generated by sensors 46a or 46b constitutes or indicates the mean ribbon width of the fiber. Thus, the computer 94 generates data corresponding to mean ribbon width by calculating and storing the average amplitude of the signal received from one of the sensors 46a or 46b. Once fiber length and ribbon width have been determined by computer 94, it further calculates the aspect ratio of the fiber (length/ribbon width) which constitutes shape information. The computer 94 also records the average frequency of the signals from sensors 46a and 46b and this is further shape information because the frequency indicates the amount of low frequency convolutions in the fiber.

Figure 7:
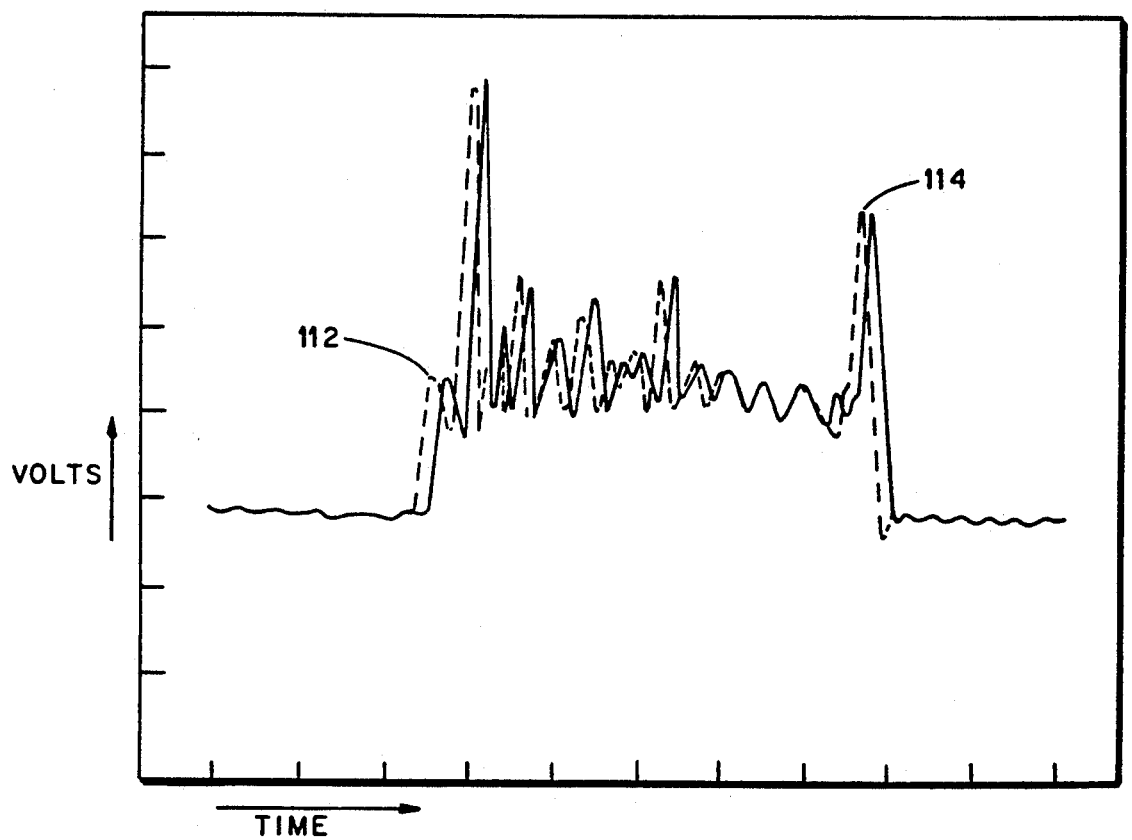
FIG. 7 is a graph showing the signals of the two extinction sensor superimposed one on the other illustrating the time delay between the two signals.

It will be noted that both FIGS. 6 and 7 show increasing voltages in the presence of a fiber 56 in the light beam 34 and in front of the sensors 46a and 46b. In reality, the amount or intensity of the light on the sensors 46a and 46b is decreased by the presence of a fiber 56 in front of the sensors. However, for clarity of illustration and display, the conditioning electronics inverts the signals so that a decreasing signal from sensors 46a and 46b is represented by an increasing signal on the display 92 which is preferably an oscilloscope.

The system shown in FIG. 5 is particularly useful for measuring characteristics of cotton fibers one-at-a-time. Because cotton is so complex, numerous parameters have been used to describe its cross sectional characteristics. Those relevant to this discussion include Dr=ribbon width, A=cross sectional area (with or without lumen), $\theta$=circularity ratio=A divided by area of a circle with the same perimeter P, and Mic=micronaire air flow permeability. Other parameters include F=Fineness or linear density, measured in gm/Km=tex, and M=Maturity. Maturity is measured in several ways, all of which more or less relate to the biological maturity in wall thickness t of the fiber at harvest. From basic fiber physics, F=pA, where p is cellulosic density, gm/cm$^3$ and $\theta$ is the most direct measure of maturity M. Thus, F is directly proportional to A and $\theta$ is directly proportional to M.

Experimentally and theoretically the following conclusions may be drawn regarding the system of FIG. 5:

1. The forward scattering signal of sensor 52 ($V_s$) correlates more highly with fiber surface area than fiber width.

2. The extinction mode signal of either of sensors 46a or 46b ($V_e$) correlates conversely.

3. $V_s$ and $V_e$ correlate poorly and therefore provide partially independent data on cross-sectional parameters of fibers.

Based in part on these conclusions, it follows that $V_s$ and $V_e$ may be used to provide data correlating to fineness (F) and (M) maturity and to evaluate this correlation, we have compared AFIS 1 data with data obtained using Image Analyzer and micronaire methods. We have found that Image Analyzer, micronaire and AFIS 1 data obey:

$$Mic = 0.679\, V_s - 5.505,\ r^2 = 0.84 \quad (1)$$

$$V \cdot \theta = 1.218\, Mic + 2.625,\ r^2 = 0.90 \quad (2)$$

Thus, one procedure for predicting average circularity ($\theta$) and cross sectional area ($\overline{A}$) is as follows. Using equation 1, predict Mic based on $V_s$ data from AFIS 1. Use the predicted Mic value and the measured $V_e$ in equation 2 to predict $\theta$. Then using the values calculated for $\theta$ and Mic, one may determine $\overline{A}$ by solving:

$$A \cdot \theta = 0.450\, Mic^2 + 16.081\, Mic - 3.591 \quad (3)$$

Since F is proportional to A, it follows that $\overline{A}$ is also a measure of $\overline{F}$, fineness. Also, since M is proportional to $\theta$, it follows that $\theta$ is a measure of M, maturity.

Referring to FIG. 5, in practice the computer 94 records $V_s$ and $V_e$ for each fiber in addition to the other information discussed above such as length and ribbon width. After all sample fibers are tested, the computer 94 then makes the appropriate calculations to determine $\overline{A}$, $\theta$ and Mic, if desired, using $V_s$ and $V_e$.

Figure 8:
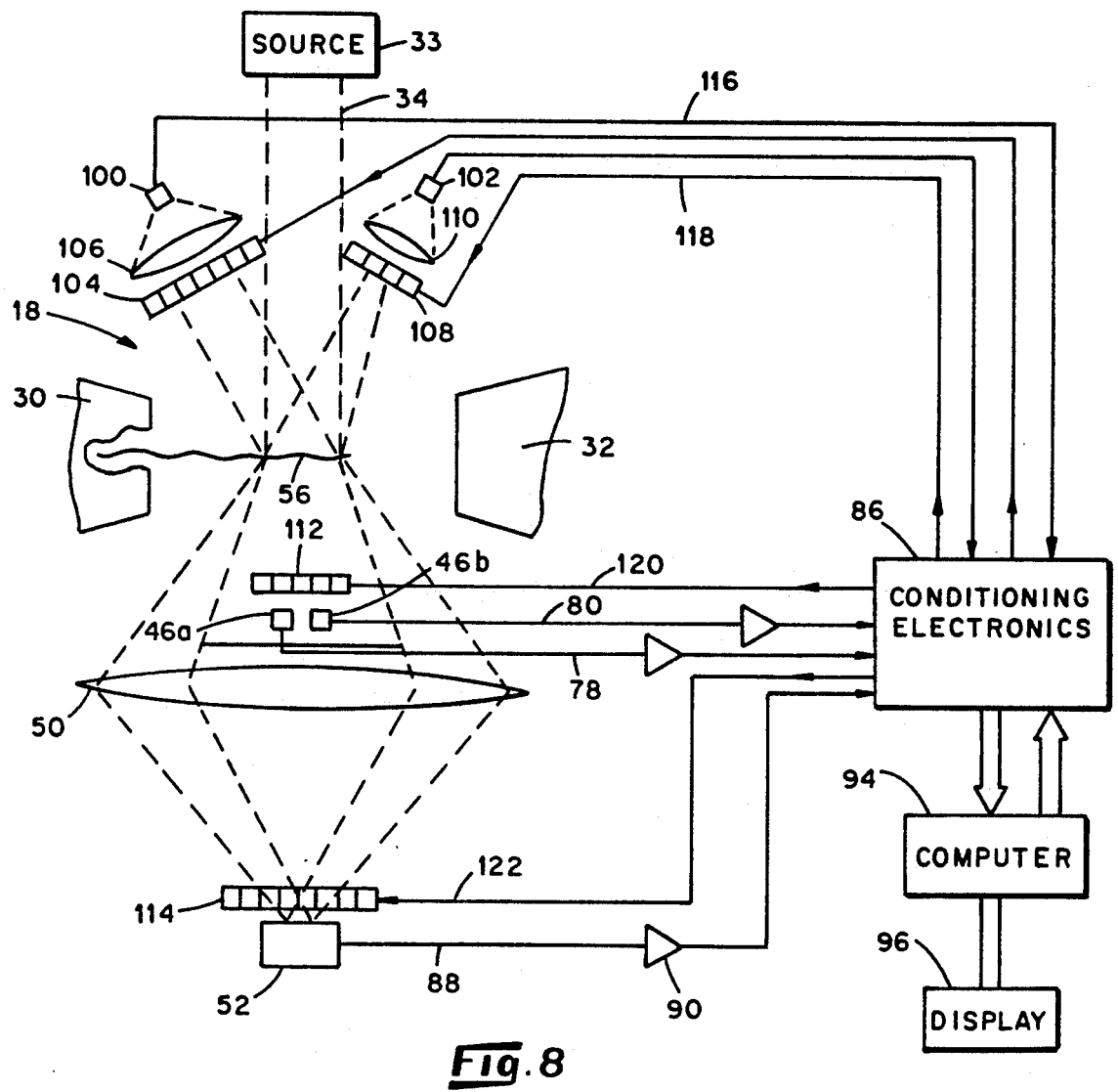
FIG. 8 is a diagrammatic view of an embodiment showing sensors for backscattered light and filters for determining color and polarization properties of the fibers.

Referring now to FIG. 8, there is shown another embodiment of the present invention in which a pair of backscattering sensors 100 and 102 are disposed to receive light that is backscattered from the beam 34 by the fiber 56. In FIG. 8, the light source 33 provides a collimated beam 34 of white light (a broad wavelength distribution) to facilitate color measurements. A filter 104 is placed in front of the detector 100 and a lens 106 is provided to focus light that is transmitted by the filter 104 onto the detector 100. In like manner, a filter 108 is disposed in front of the detector 102 and a lens 110 is provided for focusing light that is transmitted through the filter 108 onto the detector 102. A filter 112 is disposed in front of the detectors 46a and 46b and a filter 114 is positioned in front of the detector 52. Thus, all the detectors in the embodiment in FIG. 8 receive light through a filter.

The filters 104, 108, 112 and 114 are controlled by the conditioning electronics 86 and the computer 94 through lines 116, 118, 120 and 122. By applying signals through these lines, the conditioning electronics 86 may control the polarity and the wavelength responses of the filters 104, 108, 112 and 114. In this manner, the apparatus of FIG. 8 is operable to observe polarity characteristics and color characteristics produced by the fiber 56 in a forward scattering mode (filter 114 and detector 52), an extinction mode or near zero forward scattering mode (sensors 46a and 46b and filter 112), and in a backscattering mode filters 104 and 108 and detectors 100 and 102). Although all of the filters may be used to detect color or polarization information, it is preferred to use filter 104 and detector 110 to observe the grayness of cotton fibers and it is preferred to use filter 108 and detector 102 to observe the yellowness of cotton fibers. Also it is preferred to observe polarity information primarily through filters 112 and 114 and detectors 46a and 46b and 52. The information concerning grayness, yellowness and polarity is transmitted through the conditioning electronics and stored in the computer 94 for each fiber tested.

From the foregoing, it will be appreciated that the present invention is capable of very accurately measuring the speed of a fiber and using the speed to calculate the length of the fiber. In addition, using light extinction information, the mean ribbon width is rapidly determined and, using forward scattered light information, a surface data signal is generated that is indicative of fiber surface properties. In particular, it is known that the surface data signal ($V_s$) is directly related to micronaire and, using formulas 1, 2 and 3, $\theta$ and $\overline{A}$ may be calculated. Thus, the present invention is capable of analyzing single fibers from a sample with rapidity and, since characteristics of each fiber are measured, multivariate data is generated by computer 94. For example, in addition to length distribution for a sample, the computer calculates length vs. diameter distribution for the sample and may also calculate other multivariate distributions based on any of the characteristics measured such as color, shape, micronaire, $\overline{A}\theta$ or others.

What is claimed is:

1. An apparatus for rapidly measuring the properties of single entities having a size comparable to that of textile fibers and neps, each entity having a length (major axis) and at least first and second physical features spaced apart one from the other along the entity length, said apparatus comprising:
   a source of single entities:
   a first conduit for transporting said single entities;
   a second conduit for receiving and transporting said single entities from said first conduit;
   an opening formed between said first and second conduits;
   a fluid stream formed within said first and second conduits, traversing said opening, and creating a fluid flow in said conduit;
   means for delivering single entities one at a time from said source to said fluid stream, said entities being transported by said fluid stream;
   fluid flow control means for presenting the entities in a desired position; and
   sensor means disposed proximately to said opening in said conduit for optically sensing each entity as it traverses said opening and determining the speed of each entity based on said sensing, said sensor means comprising a single light beam directed through said opening, across said fluid stream, and impinging upon the entities in said fluid stream, and light sensor means disposed adjacent said opening for sensing the presence of entities as the entities are transported by said fluid flow across said opening.

2. The apparatus of claim 1 wherein said means for orienting further comprises an accelerating nozzle for accelerating the fluid and entities immediately upstream of said opening to thereby orient and straighten the entities.

3. The apparatus of claim 1 wherein said sensor means comprises:
   means for detecting when the leading end of each entity passes a first point in said opening;
   means for detecting when the leading end of each entity passes a second point in said opening downstream of the first point;
   means for detecting when the trailing end of each entity passes the first point in said opening;
   means for detecting when the trailing end of each entity passes the second point in said opening;
   means for determining a leading time for each entity passing said opening, the leading time corresponding to the time required for the leading end of each entity to pass from the first point to the second point;
   means for determining a trailing time for each entity passing said opening, the trailing time corresponding to the time required for the trailing end of each entity to pass from the first point to the second point; and means for determining the speed of each entity based on the leading time and the trailing time.

4. The apparatus of claim 1 wherein said light beam comprises a collimated beam of light.

5. The apparatus of claim 1 wherein:
said light beam comprises a collimated beam of light; and
said light sensor means comprises a first light sensor for receiving light from said collimated beam of light and a second light sensor for receiving light from said collimated beam of light, said first and second light sensors being dimensioned and positioned to detect the extinction of light caused by said entities passing through said collimated beam of light.

6. The apparatus of claim 1 wherein said light sensor means further comprises a first light sensor dimensioned and positioned to detect the extinction of light caused by entities passing through said light beam and a second light sensor positioned and dimensioned to detect forward scattered light caused by said entities passing through said light beam.

7. The apparatus of claim 1 wherein said light sensor means comprises first and second light sensors positioned side-by-side for sensing a physical feature of an entity while that entity travels a distance on the order of a millimeter and for making a speed determination based at least in part on said sensing of the physical feature.

8. The apparatus of claim 1 wherein said sensor means further comprises:
first light sensor means disposed proximately to the opening for sensing forward scattered light that is scattered by each entity as it passes through the opening and for generating a scattered light signal (Vs);
means responsive to the scattered light signal for generating surface property data corresponding to surface properties of the entities passing through the opening; and
second light sensor means for measuring light extinction caused by the fiber in the opening and for generating an extinction signal (Ve).

9. An apparatus for rapidly measuring the properties of single entities having a size comparable to that of textile fibers and neps, each entity having a length (major axis) and at least first and second physical features spaced apart one from the other along the entity length, said apparatus comprising:
a source of single entities;
a fluid stream having a fluid flow;
means for delivering a single entities one at a time from said source to said fluid stream;
means for orienting the entities so that each entity along the entity length is generally parallel with the direction of the fluid flow, has a leading entity end and has a trailing entity end;
a sample region disposed in the fluid stream downstream of said orienting means;
a collimated beam of light disposed to pass through said sample region;
first light sensor means disposed adjacent to said sample region for receiving light from the collimated beam of light;
second light sensor means disposed adjacent to said sample region for receiving light from the collimated beam of light, said first and second light sensor means being dimensioned and positioned to detect the extinction of light caused by entities passing through said sample region;
third light sensor means disposed adjacent to said sample region and being dimensioned and positioned for receiving forward light scattering caused by entities passing through said sample region.

10. The apparatus of claim 9 wherein said first and third light sensors produce signals, and further comprising means for calculating circularity ($\theta$) based on signals from the first and third light sensor means for each entity.

11. The apparatus of claim 9 wherein said first and third light sensors produce signals, and further comprising means for calculating average cross-sectional area (A) based on signals from the first and third light sensor means for each entity.

12. An apparatus for rapidly measuring the properties of single entities having a size comparable to that of textile fibers and neps, each entity having a length and two ends, said apparatus comprising:
a source of single entities;
means for separating and delivering single entities from the source to a entity output;
a first conduit having first and second ends and being disposed for receiving entities from the entity output into the first end of the first conduit;
an accelerating nozzle disposed on the second end of the first conduit;
a sample chamber disposed adjacent to said accelerating nozzle;
suction means for applying suction to the sample chamber to create a fluid stream flowing at a flow rate from said separating and delivering means through the first conduit and through the sample chamber, whereby entities are drawn through the first conduit, accelerated through the nozzle and transported through the sample chamber, said nozzle and flow rate being dimensioned so that said entities are straightened and aligned by the acceleration of the nozzle and the entities are aligned along their length to be parallel with the direction of the fluid flow;
a collimated beam of light disposed to pass through said sample chamber;
first light sensor means disposed adjacent to said sample chamber for receiving light from the collimated beam of light; and
second light sensor means disposed adjacent to said sample chamber for receiving light from the collimated beam of light, said first and second light sensor means being dimensioned and positioned to detect the extinction of light caused by entities passing through said sample chamber.

13. The apparatus of claim 12 wherein said suction means further comprises a decelerating nozzle positioned adjacent to and spaced apart from said accelerating nozzle by a predetermined distance, said decelerating nozzle receiving fluid and entities from said sample chamber and accelerating nozzle.

14. An apparatus for rapidly measuring the properties of single entities, each entity having a length and two ends, said apparatus comprising:
a source of single entities;

means for separating and delivering single entities from the source to an entity output;

a first conduit having first and second ends and being disposed for receiving entities from the entity output into the first end of the first conduit;

an accelerating nozzle disposed on the second end of the first conduit;

a sample chamber disposed adjacent to said accelerating nozzle;

suction means for applying suction to the sample chamber to create a fluid stream flowing at a flow rate from said separating and delivering means through the first conduit and through the sample chamber, whereby entities are drawn through the first conduit, accelerated through the nozzle and transported through the sample chamber, said nozzle and flow rate being dimensioned so that said entities are straightened and aligned by the acceleration of the nozzle and the entities are aligned along their length to be parallel with the direction of the fluid flow;

a collimated beam of light disposed to pass through said sample chamber;

first light sensor means disposed adjacent to said sample chamber for receiving light from the collimated beam of light;

second light sensor means disposed adjacent to said sample chamber for receiving light from the collimated beam of light, said first and second light sensor means being dimensioned and positioned to detect the extinction of light caused by entities passing through said sample chamber; and third light sensor means disposed adjacent to said sample region and being dimensioned and positioned for receiving forward light scattering caused by entities passing through said sample region.

15. An apparatus for rapidly measuring the properties of single entities having a size comparable to that of textile fibers and neps, each entity having a length, width characteristics and two ends, said apparatus comprising:

a source of single entities;

a first conduit for transporting said single entities;

a second conduit for receiving and transporting said single entities from said first conduit;

an opening formed between said first and second conduits;

a fluid stream formed within said first and second conduits, traversing said opening, and creating a fluid flow in said conduits;

means for delivering single entities one at a time from said source to said fluid stream, said entities being transported by said fluid stream;

means for orienting the entities so that each entity along the entity length is generally parallel with the direction of the fluid flow, has a leading entity end and has a trailing entity end;

a single collimated beam of light directed through said opening and across said fluid stream such that said collimated beam of light will impinge upon single entities passing said opening;

at least one sensor for receiving light after the light impinges upon said single entities and for generating a sensor signal from one sensor corresponding to the width characteristics of each entity, said light sensor being disposed for measuring light extinction caused by entities passing said opening and through said single collimated light beam; and output means responsive to the sensor signal for generating extinction data corresponding to the light extinction caused by single entities passing said opening and through said single collimated light beam.

16. The apparatus of claim 15 further comprising means for calculating the mean diameter of each entity passing said opening and through said single collimated light beam based upon the extinction data.

17. An apparatus for rapidly measuring the properties of single entities having a size comparable to that of textile fibers and neps, each entity having a length (major axis) and at least first and second physical features spaced apart from the other along the entity length, said apparatus comprising:

a source of single entities;

a conduit for transporting said single entities;

an opening formed in said conduit;

a fluid stream formed within said conduit, traversing said opening, and creating a fluid flow;

means for delivering single entities one-at-a-time from said source to said fluid stream said entities being transported by said fluid stream;

means for orienting the entity so that each entity along the entity length is generally parallel with the direction of the fluid flow, has a leading entity end and has a trailing entity end;

means for detecting when the first physical feature of each entity passes a first point in said opening in said conduit;

means for detecting when the first physical feature of each entity passes a second point in said opening in said conduit downstream of the first point;

means for detecting when the second physical feature of each entity passes the first point in said opening in said conduit;

means for detecting when the second physical features passes the second point in said opening in said conduit;

means for determining a first time for each entity passing said opening in said conduit, the first time corresponding to the time required for the first physical feature of each entity to pass from the first point to the second point;

means for determining a second time for each entity passing said opening in said conduit, the second time corresponding to the time required for the second physical feature of each entity to pass from the first point to the second point; and means for producing movement data as to each entity based upon the first time and the second time.

18. The apparatus of claim 17 further comprising means for determining the speed of each entity based upon the first time and the second time.

19. The apparatus of claim 17 further comprising means for determining the acceleration of each entity based upon the first time and the second time.

20. The apparatus of claim 17 wherein the first physical feature is the leading end of each entity and the second physical feature is the trailing end of each entity.

* * * * *